(12) United States Patent
Fogarty et al.

(10) Patent No.: US 11,460,463 B2
(45) Date of Patent: Oct. 4, 2022

(54) METHOD AND APPARATUS FOR CALCULATING DERIVED CETANE NUMBERS

(71) Applicant: Icon Scientific Limited, Bath (GB)

(72) Inventors: Kevin Fogarty, Bath (GB); David Thompson, Bath (GB); Noel Beauchamp, Bath (GB)

(73) Assignee: Icon Scientific Limited

( * ) Notice: Subject to any disclaimer, the term of this patent is extended or adjusted under 35 U.S.C. 154(b) by 0 days.

(21) Appl. No.: 17/287,620

(22) PCT Filed: Oct. 22, 2019

(86) PCT No.: PCT/GB2019/053004
§ 371 (c)(1),
(2) Date: Apr. 22, 2021

(87) PCT Pub. No.: WO2020/084293
PCT Pub. Date: Apr. 30, 2020

(65) Prior Publication Data
US 2021/0311013 A1    Oct. 7, 2021

(30) Foreign Application Priority Data
Oct. 22, 2018  (GB) ..................... 1817170

(51) Int. Cl.
   *G01N 33/28*   (2006.01)
   *G01N 7/06*    (2006.01)
   *G01N 31/12*   (2006.01)
(52) U.S. Cl.
   CPC ........... *G01N 33/2829* (2013.01); *G01N 7/06* (2013.01); *G01N 31/12* (2013.01)
(58) Field of Classification Search
   CPC ....... G01N 33/2829; G01N 7/06; G01N 31/12
   See application file for complete search history.

(56) References Cited

U.S. PATENT DOCUMENTS

| 7,949,471 B2 | 5/2011 | Ritz |
| 10,697,915 B1 * | 6/2020 | Junaedi ................... G01N 33/22 |

(Continued)

FOREIGN PATENT DOCUMENTS

WO    2008/070037    6/2008

OTHER PUBLICATIONS

Transmittal of the International Search Report and the Written Opinion of the International Search Authority—The European Patent Office—dated Mar. 10, 2020 for International Application No. PCT/GB2019/053004, 11 pages.

(Continued)

*Primary Examiner* — Brian R Gordon
*Assistant Examiner* — Dwan A Gerido
(74) *Attorney, Agent, or Firm* — Jackson Walker LLP

(57) ABSTRACT

A method and apparatus for calculating the derived cetane number of a liquid hydrocarbon sample is disclosed. The method comprises combusting (19) the sample in a constant volume combustion chamber (45). The method comprises obtaining (23) a pressure versus time combustion profile (69) of the sample wherein the profile comprises a first region (81) and a second region (83), the first region (81) including the start of combustion, and the second region (83) relating to a later time than the first region. The method comprises selecting a single data point from the second region (83) of the combustion profile (69), said data point representing a combustion delay (CD) of the combustion profile; and calculating a derived cetane number for the sample using the time value associated with said single data point.

11 Claims, 5 Drawing Sheets

(56) References Cited

U.S. PATENT DOCUMENTS

| | | | | |
|---|---|---|---|---|
| 2007/0083319 A1* | 4/2007 | Wilharm | ............ | G01N 33/2829 701/102 |
| 2008/0213914 A1* | 9/2008 | Ritz | ........................ | G01N 31/12 436/139 |
| 2008/0257017 A1* | 10/2008 | Ritz | ................... | G01N 33/2829 73/35.02 |

OTHER PUBLICATIONS

Sengar, et al., "Performance Evaluation of a Diesel Engine with Varying Shims Configuration for Different Blends of Diesel and Ethanol Introduction", International Journal of Automobile Engineering Research and Development, vol. 6, No. 4, Jul. 11, 2016, 11 pages.

Kuszewski, et al., "Use of the constant volume combustion chamber to examine the properties of autoignition and derived cetane number of mixtures of diesel fuel and ethanol", vol. 200, Jul. 1, 2017, pp. 564-575. (Abstract).

GB Search Report mailed from the UK Patent Office dated May 15, 2019 for Application No. GB1817170.2, 4 pages.

Kuszewski, et al., "Use of the constant volume combustion chamber to examine the properties of autoignition and derived cetane number of mixtures of diesel fuel and ethanol", Elsevier—Fuel, vol. 200, Jul. 1, 2017, pp. 564-575.

Diesel Fuel—"Ignition Quality Tester (IQT)", R&D 2001 Award, 4 pages.

Allard, et al., "Diesel Fuel Ignition Quality as Determined in the Ignition Quality Tester (IQT)", SAE International, International Spring Fuels & Lubricants Meeting, May 6-8, 1996, 7 pages, Part 1.

Allard, et al., "Diesel Fuel Ignition Quality as Determined in the Ignition Quality Tester (IQT)—Part II", SAE International, International Spring Fuels & Lubricants Meeting, May 5-8, 1997, 12 pages, Part 2.

Allard, et al., "Analysis of the Ignition Behaviour of the ASTM D-613 Primary Reference Fuels and Full Boiling Range Diesel Fuels in the Ignition Quality Tester (IQT)—Part III", SAE International, International Fall Fuels & Lubricants Meeting and Exposition, Oct. 25-28, 1999, 10 pages, Part 3.

Allard, et al., "Diesel Fuel Ignition Quality as Determined in the Ignition Quality Tester (IQTTM)—Part IV", SAE International, International Fall Fuels & Lubricants Meeting and Exposition, Sep. 24-27, 2001, 12 pages, Part 4.

"Standard Test Method for Cetane Number of Diesel Fuel Oil", ASTM Int'l Designation: D 613-95, 2018, 29 pages.

"Standard Test Method for Determination of Ignition Delay and Derived Cetane Number (DCN) of Diesel Fuel Oils by Combustion in a Constant Volume Chamber", ASTM Int'l Designation: D 6890-04,2018, 15 pages.

"Standard Test Method for Determination of Ignition Delay and Derived Cetane Number (DCN) of Diesel Fuel Oils by Combustion in a Constant Volume Chamber", ASTM Int'l Designation: D 6890-03a, 2018, 14 pages.

Ryan, et al., "Diesel Fuel Ignition Quality as Determined in a Constant Volume Combustion Bomb", SAE International, SAE Technical Paper Series, International Congress and Exposition, Feb. 23-27, 1987, 19 pages.

Naser, et al., "Estimating fuel octane numbers from homogeneous gas-phase ignition delay times", Elsevier-Combustion and Flame, vol. 188, 2018, pp. 307-323.

Naser, et al., "Ignition delay time sensitivity in ignition quality tester (IQT) and its relation to octane sensitivity", Elsevier—Fuel, vol. 233, 2018, pp. 412-419.

\* cited by examiner

METHOD AND APPARATUS FOR CALCULATING DERIVED CETANE NUMBERS

RELATED APPLICATIONS

The present application claims benefit of and priority to Great Britain Patent Application 1817170.2, filed Oct. 22, 2018 and PCT/GB2019/053004, filed Oct. 22, 2019, each of which is hereby incorporated by reference for all purposes, as if set forth herein in its entirety.

FIELD OF THE INVENTION

The present invention relates to a method of measuring and calculating the derived cetane number of liquid hydrocarbon samples such as middle distillate fluids or fuels, and apparatus for performing such a method.

BACKGROUND OF THE INVENTION

Methods and systems for measuring the derived cetane numbers of hydrocarbon samples are typically either based on engine data or use data from constant volume combustion chambers.

Standard methods are known for measuring derived cetane numbers using constant volume combustion chambers. The ASTM D6890-03a standard describes a method of measuring derived cetane numbers using a constant volume combustion chamber. In this method, the cetane number is determined from an equation that uses a single data point from a combustion pressure versus time profile. The selected data point represents an ignition delay of a sample.

EP2087346 discloses a method of calculating a cetane value using a combustion chamber. This method selects a plurality of the data points from combustion pressure curves for a sample, with each data point representing an ignition delay. A derived cetane value is calculated from a power series expansion equation, expanded about each of the selected data points.

The more recent ASTM D7668-14a standard provides an alternative method of calculating derived cetane numbers of diesel fuel oils. This standard uses data points representing both the ignition delay and the combustion delay in a multivariate equation in order to determine the derived cetane number. Thus, in recent times the trend in this field has been to increase the number of points from the pressure-time profile that are used in the calculation of cetane number in order to improve the quality of the cetane number calculation.

Known methods such as those described above can have high levels of uncertainty, as the derived cetane number may be dependent upon proportions of fast and slow burning fuel components in the sample, and the value of the data point may be dependent upon the capability of the apparatus to differentiate fast and slow burn fuel components. It generally necessary to repeat the measurement of the combustion profile through multiple cycles for each sample in order to determine average ignition delay and combustion delay values, in order to reduce this uncertainty. Therefore there remains a need in the field to develop more efficient and accurate methods of calculating derived cetane values.

SUMMARY OF THE INVENTION

The present invention comprises a method of calculating the derived cetane number of a liquid hydrocarbon sample, according to claim 1. The method comprises injecting a sample into a combustion chamber, the combustion chamber being held at a constant volume, and combusting the sample in the combustion chamber. The pressure in the constant volume combustion chamber is measured as a function of time after the injection until combustion is completed, and a pressure versus time combustion profile of the sample that is injected into said constant volume combustion chamber is obtained. The combustion profile comprises a first region and a second region, the first region including the start of combustion, and the second region relating to a later time than the first region. A single data point from the second region of the combustion profile is selected, said data point representing a combustion delay of the combustion profile. A derived cetane number for the sample is calculated using the time value associated with said single data point.

As the present method uses a combustion delay value to calculate the derived cetane number for the sample the effect of fast burning fuel components may have a reduced impact on the value of cetane number calculated. Thus, the present invention may provide a more accurate calculation of cetane number than methods using the ignition delay value. The present method may be more efficient than known methods that use both ignition delay and combustion delay values, as the present method only requires a single data point to be extracted from the combustion pressure profile.

The liquid hydrocarbon sample may be a diesel fuel oil, or a middle distillate fluid or fuel. The sample may undergo preparation prior to injection into the chamber, for example, the sample temperature may be increased and/or the sample pressure may be increased using a fuel pressure amplifier.

The chamber volume is constant during the measurement of a pressure time combustion profile for a sample. The temperature of the chamber may be measured and controlled using a control system comprising a temperature sensor or thermocouple. The temperature of the combustion chamber wall may be measured using a thermocouple, which may, for example, be provided on the interior wall of the chamber. The temperature of the chamber may be held at a temperature between about 570 and 660° C.

Prior to injection of a sample, the chamber pressure may be measured using a pressure sensor. If the chamber pressure is not at an ambient level, an exhaust valve may be opened to de-pressurise the chamber.

The chamber pressure may be brought to a pre-determined pressure, hereafter referred to as the pre-injection pressure, prior to injection of the sample. This pre-injection pressure may be about 100 kPa. The pre-injection pressure may be reached by opening a chamber inlet valve and increasing the chamber pressure to, for example, 90 kPa, and then topping up the chamber pressure in small increments, for example, increments of 10 kPa.

Once the pre-injection pressure has been reached, the chamber inlet valve may be closed, and the chamber temperature and pressure may be allowed to stabilise for a fixed period of time before fuel injection. The chamber pressure may be monitored to check for leaks in the chamber prior to injection of the sample. The chamber pressure may be monitored using a pressure sensor. If a leak is evident, for example, if a pressure drop is detected, an indicator or alarm may be activated.

Injection of the sample into the chamber may be controlled by a fuel injection controller. For example, once the pre-injection pressure has been reached, a fuel injection controller may send a signal to the fuel injector indicating that an injection into the combustion chamber should occur.

The fuel injection controller may control the duration of the injection and/or the volume of sample injected into the chamber.

After injection of a sample, the sample is combusted in the combustion chamber. A combustion pressure sensor may be used to measure the combustion pressure profile. The combustion pressure profile may be recorded using a sound-card, for example, a commercially available soundcard, which detects a voltage signal from the combustion pressure sensor. Alternatively, any other suitable data acquisition method may be used to record the pressure in the chamber as a function of time.

The combustion profile may be recorded and analysed using any suitable software. The combustion profile may be visually represented, for example as a graph of pressure versus time. The combustion pressure profile may be represented on a display, for example, a user interface.

The combustion profile comprises a first region and a second region. The first region includes the start of combustion. The first region may include the ignition delay (ID) time period. The ID time period may be defined as the elapsed time between injection of a sample, and the time at which combustion of the sample begins. The time at which combustion begins may be defined as the time at which the pressure in the combustion chamber reaches a predetermined value above the pre-injection chamber pressure. For example, the point at which the measured pressure is 20 kPa above the pre-injection chamber pressure. Therefore the ignition delay time may be the time at which the pressure in the combustion chamber reaches a value $P_{ID}=P_0+20$ kPa, where $P_0$ is the pre-injection pressure. Alternatively, the time at which combustion begins may be taken as the time at which the pressure in the combustion chamber returns to the pre-injection pressure ($P_0$) following the initial drop in pressure. The second region corresponds to a later time than the first region. The second region may include the time between the end of the ID time period and the time at which combustion of the sample is complete. The method may comprise not selecting a data point from the first region.

A single data point is selected from the second region of the combustion profile, said data point representing the combustion delay (CD) time. The combustion delay may be defined as the elapsed time between injection of the sample, and the time at which the midpoint of the net pressure increase of the combustion pressure curve is reached. The CD may be defined as the time at which $P_{CD}$ is reached, where $P_{CD}=(P_0+P_{max})/2$, where $P_{max}$ is the maximum pressure recorded during combustion of the sample.

The derived cetane number, CN, may be calculated using an equation of the form $$CN = x_1 CD^{y_1} + x_2 CD^{y_2} + \ldots + x_n CD^{y_n}$$

where $x_1$, $x_2$ and $x_n$ are constant coefficients, $y_1$, $y_2$ and $y_n$ are powers of CD and CD is the time value representing the combustion delay. The coefficients $x_1$, $x_2$ and $x_n$, and the powers $y_1$, $y_2$ and $y_n$, may be empirically determined or semi-empirically determined. These coefficients/powers may be determined, at least in part, by calibrating the combustion chamber. These coefficients/powers may be determined, at least in part, by testing samples having a known cetane value and using curve-fitting techniques, e.g. regression analysis, to identify the coefficients/powers that provide a value acceptably close to that known cetane value when used in the present method.

The derived cetane number, CN, may be calculated using an equation of the form $$CN = x_1 + \frac{x_2}{CD^{1.5}} - x_3 CD$$

where $x_1$, $x_2$ and $x_3$ are constant coefficients and CD is the time value representing the combustion delay. The coefficients $x_1$, $x_2$ and $x_3$ may be empirically determined or semi-empirically determined. These coefficients may be determined, at least in part, by calibrating the combustion chamber. These coefficients may be determined, at least in part, by testing samples having a known cetane value and using curve-fitting techniques, e.g. regression analysis, to identify the coefficients that provide a value acceptably close to that known cetane value when used in the present method.

After measurement of the combustion profile for the sample, at least one additional injection of the sample into the combustion chamber may be performed. At least two further injections of the sample may be made at timed intervals after measuring the combustion profile of the sample. These additional injections may be controlled by a fuel injection controller, and maybe made at intervals of around 2 seconds. Sample that is injected during these additional injections will not be combusted.

After measurement of the combustion profile for the sample, the chamber may be flushed prior to any subsequent combustion profile measurements. For example the chamber may be flushed using a fluid that is not the sample, for example air. Flushing the chamber in this manner has been found to reduce the number of combustion cycles required to obtain an accurate derived cetane number for a sample.

The method of the present disclosure may further comprise the step of calibrating the combustion chamber by measuring the combustion profile of a reference sample. Using methods of the present disclosure, a derived cetane number for the reference sample may be determined.

The coefficients $x_1$, $x_2$ and $x_3$ may be determined using the calibration of the combustion chamber. Values for the coefficients $x_1$, $x_2$ and $x_3$ may be determined from this calibration measurement, by comparing the derived cetane number for the reference sample calculated using methods of the present disclosure to a pre-determined cetane number of the reference sample.

The reference sample used for calibration may be a primary reference sample with a known cetane value. An initial calibration of the chamber may be performed prior to injection of a sample. This initial calibration may use a primary reference sample. Further calibration checks may be made after measuring the combustion profile of a sample, and may be made before the injection and combustion of a subsequent sample. The reference sample used for further calibration checks may be a secondary reference sample, wherein the cetane number of the secondary reference sample has been pre-determined using a lab based analyser. Further calibration checks using secondary reference samples may be advantageous in reducing the need for calibration checks that use expensive primary reference fuels.

The difference between coefficients $x_1$, $x_2$ and $x_3$, calculated using secondary reference samples and coefficients calculated during the initial calibration of the chamber may be determined.

The volume of the combustion chamber may be adjusted after measuring the combustion profile of a sample. The volume of the combustion chamber may be adjusted after a calibration check. The volume of the combustion chamber may be adjusted to reduce or eliminate the difference between the cetane number calculated during initial calibration and the cetane number calculated from a subsequent calibration check. An adjustment of the volume of the combustion chamber may be performed after each combustion pressure profile measurement.

The method may further comprise performing a blockage check. Performing the blockage check may comprise opening the combustion chamber, measuring the pressure in the chamber over time until a pre-determined pressure is reached, determining the time, t1, between opening the chamber and the chamber reaching the pre-determined pressure, comparing t1 to a pre-specified threshold time, tt, and providing an indication if t1>tt. To perform the blockage check, an exhaust valve connected to the combustion chamber may be opened to depressurise the combustion chamber. The pre-determined pressure may be the ambient pressure. If the time taken to reach the pre-determined pressure exceeds a pre-specified threshold time, tt, an indicator or alert may be triggered. This alert or indicator may be provided to a user, for example, via a user interface. The alert or indicator may be an audible or visible alert, or a combination of the two.

The method steps of the present disclosure may be repeated. Combustion pressure profiles may be repeatedly measured for a liquid hydrocarbon sample. Multiple combustion pressure profiles for a sample may be recorded, and from each of these multiple combustion pressure profiles, a data point representing combustion delay may be obtained. The time values associated with these multiple data points may be averaged, and the average time value may be used to calculate a derived cetane number.

Combustion pressure profiles measured for the same liquid hydrocarbon sample may be averaged, or the values of the data point representing the combustion delay may be averaged. Alternatively, multiple values for the derived cetane number may be calculated, and may then be averaged. The steps of performing a calibration check, blockage check, injecting additional sample, performing a leak check, and adjusting the volume of the chamber may be performed in between each combustion profile, or periodically after a pre-specified number of measurements.

The method of the present invention may find particular application for measuring derived centane numbers in the range 15 to 85, for example, 25 to 75, for example 30 to 70, for example 35 to 65 inclusive.

According to another aspect, the invention comprises apparatus for measuring the derived cetane number of a liquid hydrocarbon sample. The apparatus comprises a combustion chamber, a fuel injector arranged to inject the sample into the combustion chamber, a combustion pressure sensor for measuring the pressure in the chamber over time; and a control system arranged to receive and analyse data from the combustion pressure sensor.

The control system is configured to calculate a derived cetane number for the sample using a single data point of a pressure-time profile produced using the data received from the pressure sensor, said single data point representing a combustion delay of the combustion profile. The control system may comprise software programmed to carry out one or more steps of the method of the invention.

The control system (and/or the software forming part thereof) may be configured to carry out one or more of the following steps:
control injection of a sample into the combustion chamber;
initiate combustion of a sample in the combustion chamber;
produce a pressure versus time combustion profile for the sample;
identify first and second regions of the combustion profile;
identify a single data point from the combustion profile, said data point representing a combustion delay of the combustion profile;
calculate a derived cetane number for the sample using the time value associated with said single data point.

The apparatus comprises a fuel injector which may be a common rail fuel injector. A fuel injector controller may be used to control the fuel injector. A fuel pressure amplifier may be used to increase the fuel pressure prior to injection. The fuel injector may be cooled, for example, using a cooling passage provided through the chamber wall.

The apparatus comprises a combustion pressure sensor for measuring the pressure as a function of time in the chamber during combustion. The apparatus may comprise a further pressure controller for measuring and controlling the pressure in the chamber prior to injection of the sample and/or in between measurements of combustion pressure curves.

The apparatus comprises a control system arranged to receive and analyse data from the combustion pressure sensor. The control system may be housed in an electronics enclosure. The control system may comprise software for recording and analysing the pressure combustion curve. The control system may be connected to interactive screens to enable user control of the apparatus.

The control system may be pre-programmed with coefficients, for example, $x_1$, $x_2$ and $x_3$ for deriving the cetane number from the combustion profile. These coefficients may be determined from a calibration of the combustion chamber using calibration methods of the present disclosure.

A set of shims may be provided with the apparatus. The shims may be configured to enable the volume of the combustion chamber to be adjusted, and may be used for adjusting the volume of the chamber between measurements of combustion pressure profiles. The combustion chamber may be constant volume combustion chamber.

The set of shims may be configured to be mounted on the combustion chamber such that a shim reduces the volume of the combustion chamber when mounted thereon.

The combustion chamber may comprise a removable flange, which may be arranged such that when it is removed, the interior of the chamber can be inspected. The removable flange may be cooled to enable quick removal if inspection of the chamber is required. The apparatus may comprise a cooling system configured to provide a coolant to the flange. The flange may comprise one or more cooling channels formed therein such that the surface area of the flange exposed to the coolant is thereby increased. The flange may be configured to receive a shim and/or the or each shim may be configured to be mounted on the flange of the combustion chamber. For example the shim and flange may comprise a corresponding set of mounting features such that when the mounting features are engaged the shim is connected to the flange.

In use, the apparatus may be connected to a production line, for example a production line for the production of liquid hydrocarbon fuels, for example diesel fuels. The apparatus may comprise a supply line configured to provide a sample to the combustion chamber. The apparatus may comprise a bypass line. In use, fuels may flow from the production line through the bypass line (and optionally back to the production line) when the analyser is not testing a sample. The bypass line may bypass the combustion chamber. The apparatus may comprise a bypass valve arranged to divert the flow of some of all of the fuel from the supply line and/or bypass line to provide a sample for combustion in the combustion chamber. The bypass valve may provide a fluid connection between the supply line and the combustion chamber. When a sample is to be tested, the fluid is rerouted by the bypass valve to the combustion chamber. Thus, the analyser may be configured such that, in use, fluid from the production line continuously flows through the analyser, and a sample is extracted from this flow at the start of the testing cycle. Thus, samples tested by the analyser may represent the fuel as currently in the production line without any significant lag.

Elements of the apparatus of the present disclosure may be housed in one or more explosion proof boxes. One or more of the combustion chamber, the combustion pressure sensor, fuel injector, the temperature sensor and the fuel injection controller may be housed in a first explosion proof box. The control system may be housed in a second explosion proof box.

Elements of the apparatus of the present disclosure may be housed in one or more purged cells. Each purged cell may comprise an enclosure to which a supply of gas or fluid is provided so as to flush the atmosphere within the cell. One or more of the combustion chamber, the combustion pressure sensor, fuel injector, the temperature sensor and the fuel injection controller may be housed in a first purged cell, for example a cell purged with nitrogen or an inert gas or fluid. The control system may be housed in a second purged cell. This second purged cell may be purged with air.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which.

TEXT OF FIG. 1

Figure 1:
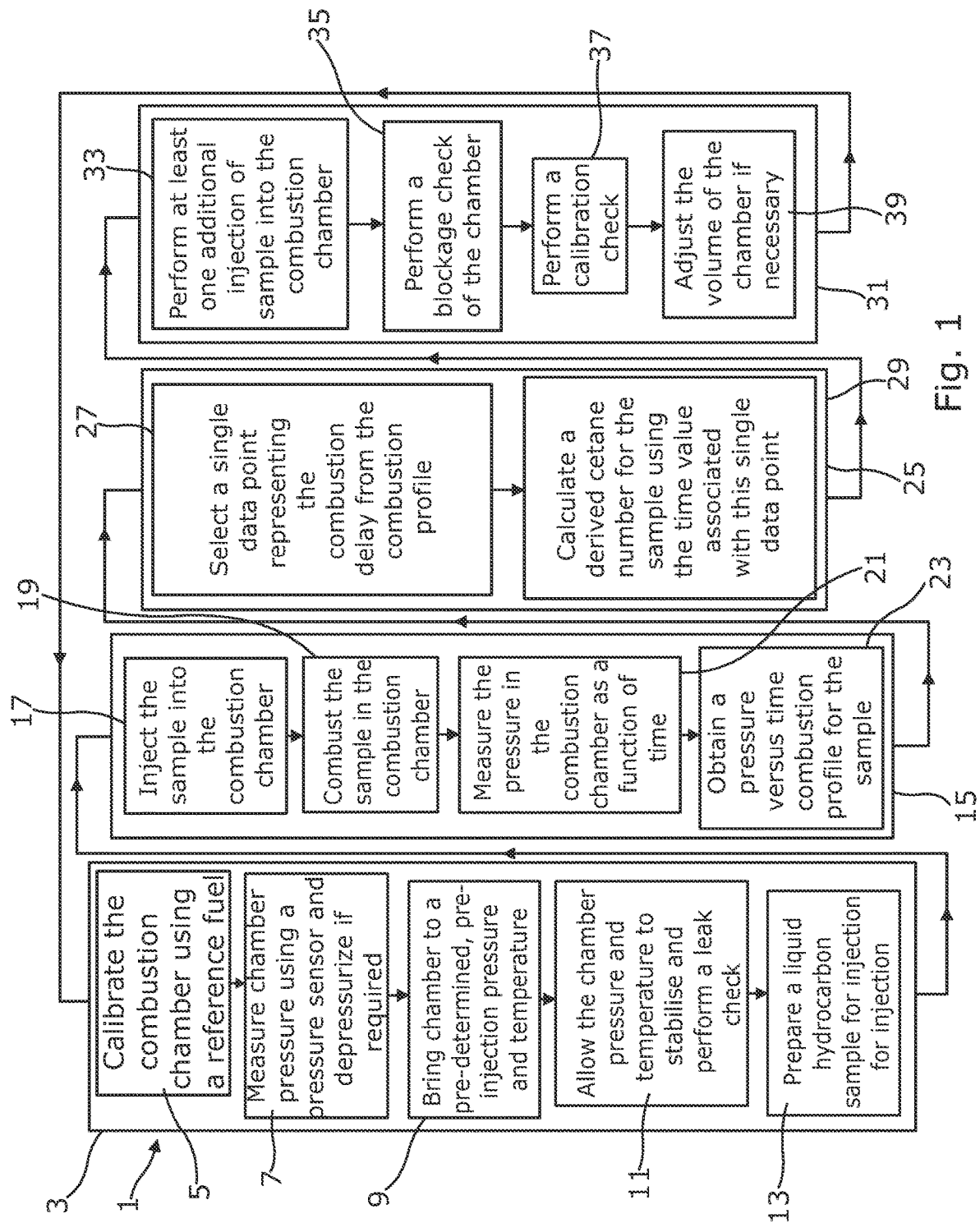
FIG. 1 shows a flow chart illustrating the steps of a method for calculating a cetane number according to an example embodiment of the invention.

With reference to the numbered boxes of FIG. 1 the text of FIG. 1 is as follows:
5: Calibrate the combustion chamber using a reference fuel.
7: Measure chamber pressure using a pressure sensor and depressurize if required.
9: Bring chamber to a pre-determined, pre-injection pressure and temperature.
11: Allow the chamber pressure and temperature to stabilise and perform a leak check.
13: Prepare a liquid hydrocarbon sample for injection for injection.
17: Inject the sample into the combustion chamber.
19: Combust the sample in the combustion chamber.
21: Measure the pressure in the combustion chamber as a function of time.
23: Obtain a pressure versus time combustion profile for the sample.
27: Select a single data point representing the combustion delay from the combustion profile.
29: Calculate a derived cetane number for the sample using the time value associated with this single data point.
33: Perform at least one additional injection of sample into the combustion chamber.
35: Perform a blockage check of the chamber.
37: Perform a calibration check.
39: Adjust the volume of the chamber if necessary.

DETAILED DESCRIPTION

An example of the apparatus of the present disclosure and the method of the present disclosure are described below.

FIG. 1 shows a flow chart (1) illustrating the steps of a method for calculating a cetane number according to an example embodiment of the invention.

Block 1 (3) of the flowchart shows method steps that are performed prior to the injection of a sample into the combustion chamber.

Prior to injection of a sample into the combustion chamber, the chamber is calibrated using a reference fuel (5). The calibration is performed using a primary reference fuel with a known cetane value.

The chamber pressure is measured prior to injection (7). If the chamber pressure is not at ambient pressure or at an accepted pre-specified pressure the chamber is de-pressurized.

The chamber pressure is brought to a pre-determined pre-injection pressure (for example 100 kPa) prior to injection of the sample (9). The pre-injection pressure is reached by increasing the chamber pressure to, 90 kPa, and then topping up the chamber pressure in small increments of 10 kPa.

Once the pre-injection pressure has been reached the chamber temperature and pressure may be allowed to stabilise for a fixed period of time before fuel injection (11). The chamber pressure is monitored to check for leaks in the chamber during this time period. If a leak is evident, for example, if a pressure drop is detected, an indicator or alarm may be activated.

A liquid hydrocarbon sample is prepared prior to injection (13), by increasing the pressure to a pre-determined pre-injection pressure. The temperature of the sample is increased also to a pre-determined value.

Block 2 (15) of FIG. 1 shows steps of injecting and combusting the sample and measuring the combustion profile.

The liquid hydrocarbon sample is injected into the combustion chamber (17), and after injection of a sample, the sample is combusted in the combustion chamber (19). Pressure in the chamber is measured as a function of time (21) to obtain a combustion profile for the sample (23). The profile will comprise a first region and a second region, with the first region including the start of combustion, and the second region relating to a later time than the first region.

Block 3 (25) of FIG. 1 shows the steps that are taken to calculate a derived cetane number for the sample from the combustion profile. A single data point representing the combustion delay is selected from the second region of the combustion profile (27).

A derived cetane number for the sample is calculated using the time value associated with this single data point (29). The derived cetane number, CN, is calculated using an equation of the form $$CN = x_1 + \frac{x_2}{CD^{1.5}} - x_3 CD$$

where $x_1$, $x_2$ and $x_3$ are constant coefficients determined from the calibration of the apparatus using a fuel sample having a known cetane value and CD is the time value representing the combustion delay. The coefficients may be determined using standard curve fitting techniques.

Block 4 (31) of FIG. 1 shows the steps that are taken after measurement of the combustion profile. After measurement of the combustion profile for a sample, at least one additional injection of the sample into the combustion chamber is performed (33), and preferably at least two further injections of the sample are be made at timed intervals. Sample that is injected during these additional injections is not combusted.

A blockage check of the chamber is also performed (35), by opening the combustion chamber and measuring the pressure in the chamber over time until a pre-determined pressure is reached. The time, t1, between opening the chamber and the chamber reaching the pre-determined pressure is determined, and is compared to a pre-specified threshold time, tt. An indication is provided if t1>tt.

A calibration check of the chamber is performed (37) using a secondary fuel, and the volume of the combustion chamber may be adjusted after measuring the combustion profile of a sample (39).

Any or all of these steps may be repeated for the same or for different liquid hydrocarbon samples. Not all of these steps may be carried out in each testing cycle, for example, a blockage check and/or calibration step may not be carried out in each cycle.

Figure 2:
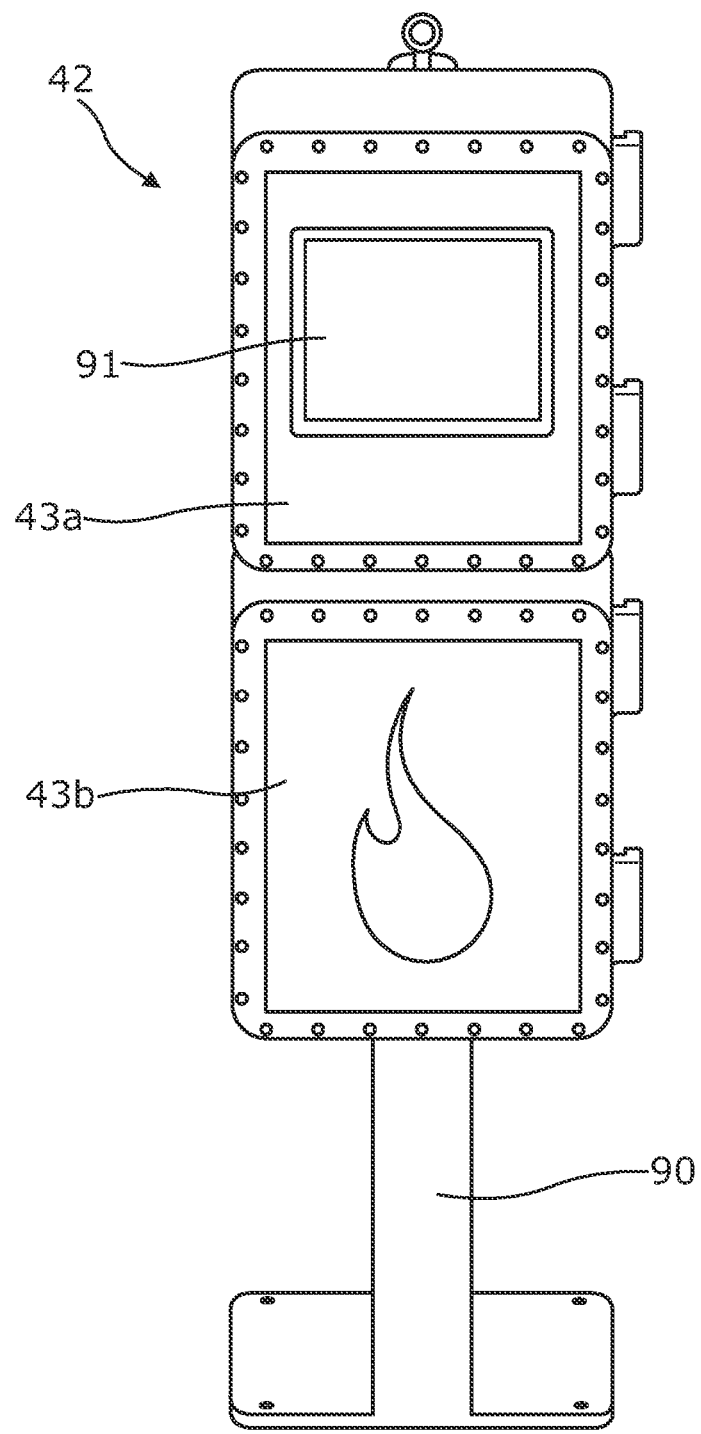
FIG. 2 shows an apparatus for measuring cetane number in accordance with an example embodiment of the invention.

FIG. 2 shows an analyser (42) for measuring cetane number in accordance with an example embodiment of the invention. The analyser (42) comprises two explosion proof enclosures (43a, 43b) mounted one on top the other on a base plate (90). The lower of the two enclosures (43b) houses an analysis cell which is shown in more detail in FIG. 3. The higher of the two enclosures (43a) houses the electronics system of the analyser (42) and is shown in more detail in FIG. 4. A touch screen (91) is mounted on the front of the upper enclosure (43a) to allow user input to control the analyser (42). In use, the analyser (42) is connected to a production line producing liquid hydrocarbon fuels.

Figure 3:
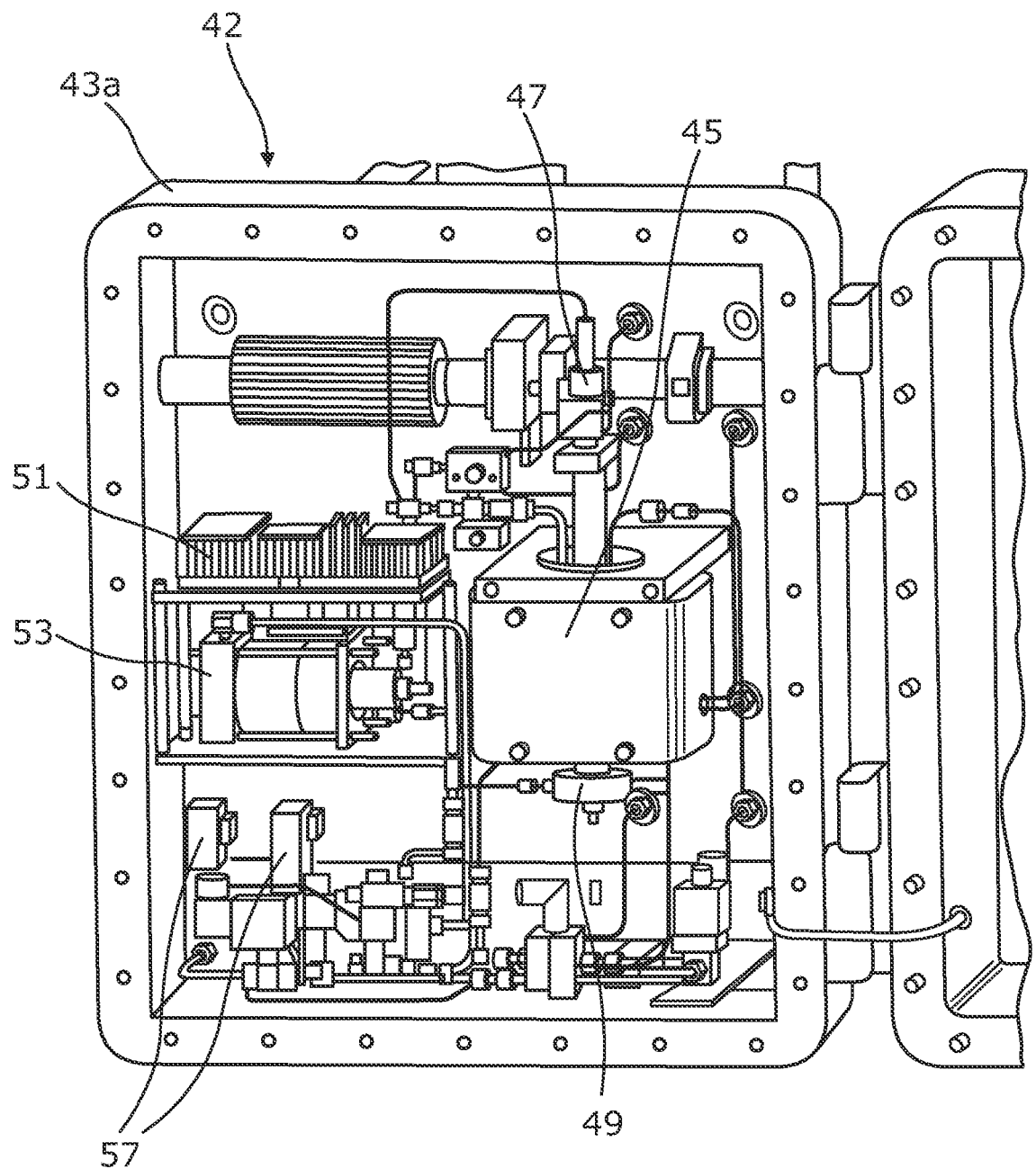
FIG. 3 shows a close up view of part of the interior of the apparatus of FIG. 2.

The lower explosion proof box (43b) is shown in the open configuration in FIG. 3. A combustion chamber (45), a fuel injector (47) arranged to inject the sample into the combustion chamber (45), and a combustion pressure sensor (49) for measuring the pressure in the chamber over time are located within the explosion proof box (43a). The apparatus further comprises a fuel injector controller (51) that is used to control the fuel injector (47) and fuel pressure amplifier (53) that is used to increase the fuel pressure prior to injection. The apparatus comprises a further pressure controller (57) for measuring and controlling the pressure in the chamber prior to injection of the sample and/or in between measurements of combustion pressure curves. The apparatus comprises a temperature sensor (not shown in FIG. 3) for measuring the temperature on the interior of combustion chamber (45). The apparatus comprises a bypass (not shown in FIG. 3) which diverts fuel around the combustion chamber. In use, when a sample is not being tested, fluid may flow through the bypass before being returned to the production line.

Figure 4:
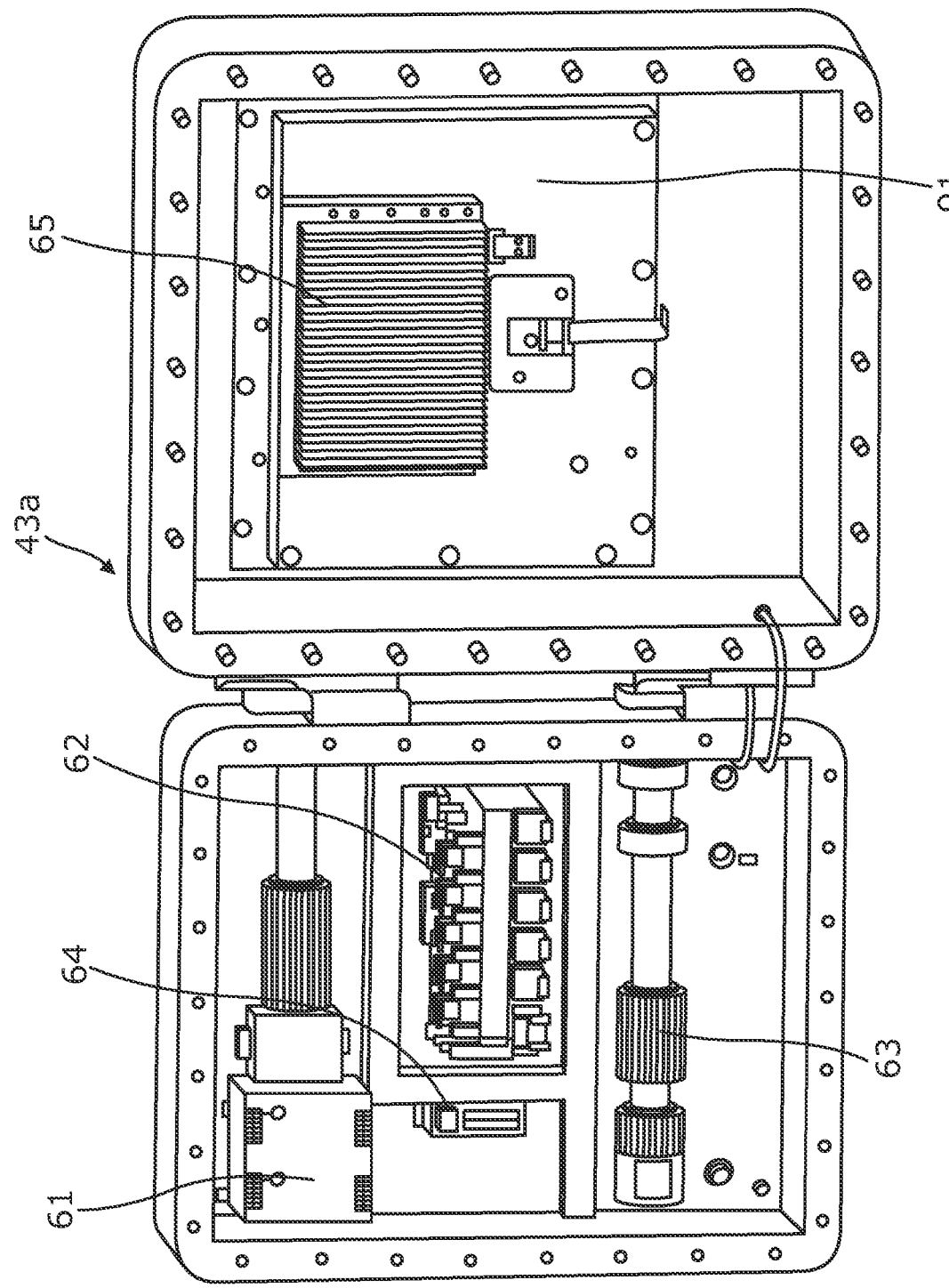
FIG. 4 shows a close up view of part of the interior of the apparatus of FIG. 2.

The upper explosion proof box (43a) is shown in the open configuration in FIG. 4. A power supply (61), input/output cards (62) including a sound card, terminal connections (63) via which electrical connections (not shown) are provided between the upper and lower enclosures (43a, 43b), and USB hub (64) are located within explosion proof box (43a) and connected to a computer (65) which is mounted to the rear of the touch screen (91). Computer (65) forms part of the control system of the analyser and includes software for recording and analysing the pressure readings received from combustion pressure sensor (49) as well as receiving input from a user and providing outputs to the user.

Figure 5:
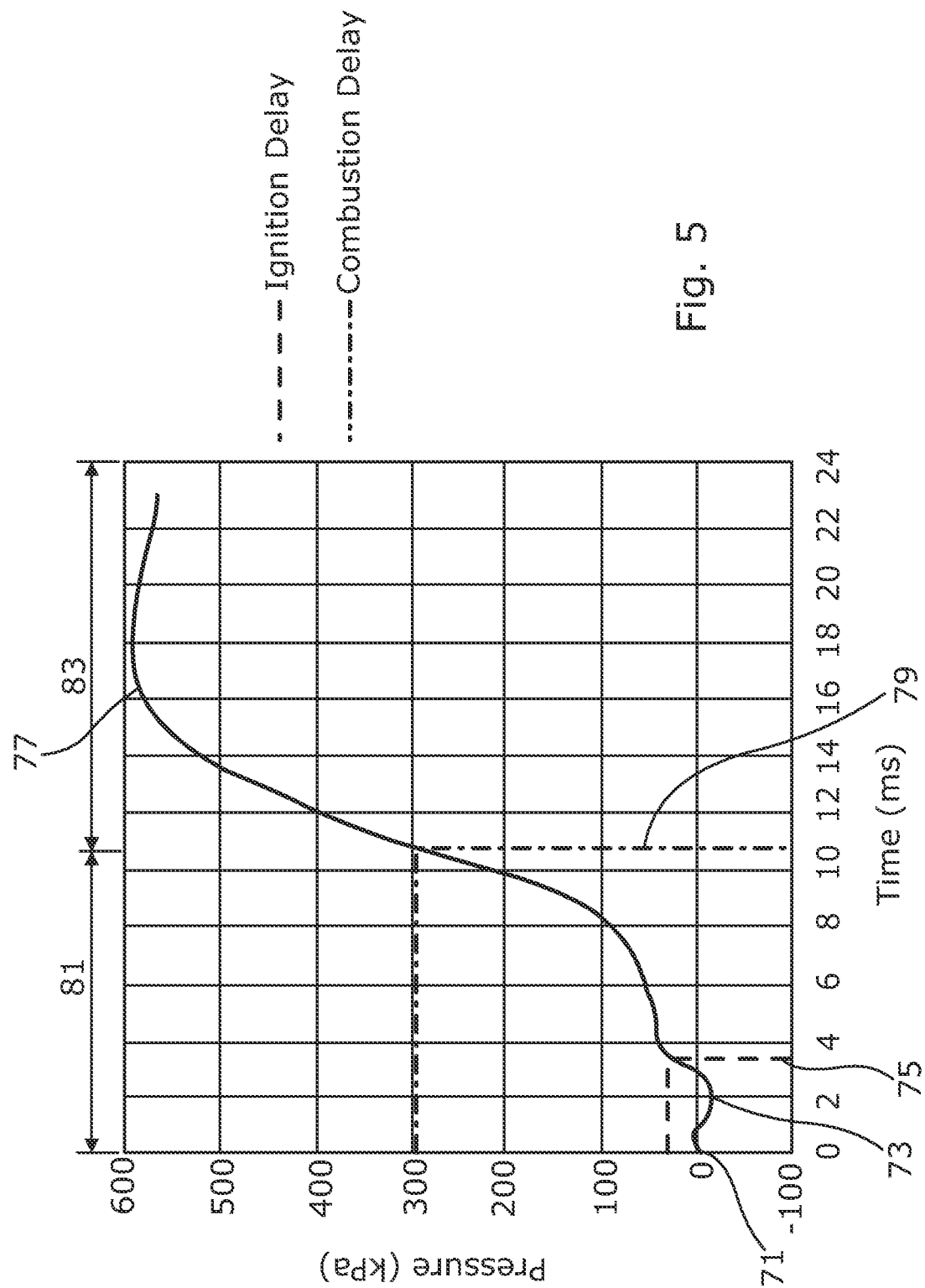
FIG. 5 shows an example combustion pressure versus time profile measured using the method of the present disclosure.

FIG. 5 shows an example combustion pressure profile (69) obtained using methods of the present invention. The profile shows the pressure measured in the combustion chamber as a function of time during combustion of a sample.

At time=0 ms, sample is injected into the combustion chamber. Prior to injection of the sample, the combustion chamber pressure may have been set to an initial value ($P_0$) (71). This pre-injection pressure may be, for example 1000 kPa. When plotting the combustion pressure profile of a sample, measured and recorded pressure values may be offset in a linear manner such that $P_0$ corresponds to a pressure of P=0 kPa.

A drop in the pressure of the combustion chamber, indicated by a dip (73) in the pressure-time curve for the sample may be measured as, or shortly after the sample is injected. The ignition delay (ID) (75) is the elapsed time between injection of the sample and the time at which combustion of the sample begins. In this case, the time at which combustion begins may be taken to be the time at which the pressure in the combustion chamber reaches a predetermined value above the pre-injection chamber pressure. In FIG. 1, the time at which combustion begins is indicated by the point ID on the curve, and is the point at which the measured pressure is 20 kPa above the pre-injection chamber pressure. Therefore the ignition delay time is the time at which the pressure in the combustion chamber reaches a value $P_{ID}=P_0+20$ kPa. In other embodiments, however, the time at which combustion begins may be taken as the time at which the pressure in the combustion chamber returns to the pre-injection pressure ($P_0$) following the initial drop in pressure.

As the sample is combusted, the pressure in the combustion chamber increases up to a maximum value ($P_{max}$) (77). Once combustion of the sample is complete, the pressure in the combustion chamber may begin to decrease. The combustion delay (CD) (79) is defined as the elapsed time between injection of the sample, and the time at which a pressure representing the midpoint of the net pressure increase of the combustion pressure curve is reached, therefore the combustion delay is indicated by the time at which the pressure in the combustion chamber reaches $P_{CD}=(P_0+P_{max})/2$.

The combustion profile comprises a first region (81) and a second region (83), the first region (81) including the start of combustion, and the second region (83) relating to a later time than the first region (81). In FIG. 5, the first region (81) encompasses the elapsed time between injection of a sample, and the time at which combustion of the sample begins. In FIG. 5 the second region encompasses the time between the end of the ID time period and the time at which combustion of the sample is complete.

In order to calculate the derived cetane value for the sample, a data point from the second region (43) that represents the combustion delay (CD), i.e. the point at which the $P_{CD}=(P_0+P_{max})/2$ is extracted from the pressure-time combustion profile and is used to calculate the derived cetane number using an equation in the form:

$$CN = x_1 + \frac{x_2}{CD^{1.5}} - x_3 CD$$

In one embodiment, the following equation is used to calculate the derived cetane number:

$$CN = 44.770 + \frac{406.925}{CD^{1.5}} - 0.252 CD$$

This equation has been found to provide accurate calculation of derived cetane number for cetane numbers in the range 35 to 65.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

For example, in the above apparatus various elements of the analyser are located within explosion proof boxes. Such elements may alternatively be located in one or more purged cells.

The invention claimed is:

1. A method of calculating a derived cetane number of a liquid hydrocarbon sample, the method comprising:
   (a) injecting a sample into a combustion chamber, the combustion chamber being held at a constant volume;
   (b) combusting the sample in the combustion chamber;
   (c) measuring a pressure in the constant volume combustion chamber as a function of time after the injection until combustion is completed;
   (d) obtaining a pressure versus time combustion profile of the sample injected into said constant volume combustion chamber, wherein the profile comprises a first region and a second region, the first region including the start of combustion, and the second region relating to a later time than the first region;
   (e) selecting a single data point from the second region of the combustion profile, said data point representing a combustion delay of the combustion profile; and
   (f) calculating the derived cetane number for the sample using the time value associated with said single data point, wherein the derived cetane number, CN, is calculated using an equation of the form $$CN = x_1 + \frac{x_2}{CD^{1.5}} - x_3 CD$$

where $x_1$, $x_2$ and $x_3$ are constant coefficients and CD is the data point representing the combustion delay.

2. The method of claim 1 further comprising the step of bringing the combustion chamber pressure to a pre-determined pre-injection pressure, prior to injection of the sample.

3. The method of claim 1, further comprising the step of monitoring the chamber pressure to check for leaks in the chamber prior to injection of the sample.

4. The method of claim 1 wherein the coefficients $x_1$, $x_2$ and $x_3$ are empirically determined.

5. The method of claim 1, further comprising the step of calibrating the combustion chamber by measuring the combustion profile of a reference sample.

6. The method of claim 1, further comprising the step of calibrating the combustion chamber by measuring the combustion profile of a reference sample, wherein the coefficients $x_1$, $x_2$ and $x_3$ are determined using the calibration of the combustion chamber, and wherein the coefficients $x_1$, $x_2$ and $x_3$ are empirically determined.

7. The method of claim 1, further comprising the step of performing at least one additional injection of the sample into the combustion chamber after measuring a combustion profile of a sample.

8. The method of claim 1, wherein the volume of the combustion chamber is adjusted after the combustion profile of a sample has been measured.

9. The method of claim 1, further comprising the step of performing a blockage check, the blockage check comprising:
   (i) opening the combustion chamber;
   (ii) measuring the pressure in the chamber over time until a pre-determined pressure is reached;
   (iii) determining the time, t1, between opening the chamber and the chamber reaching the predetermined pressure
   (iv) comparing t1 to a pre-specified threshold time, tt; and
   (v) providing an indication if t1>tt.

10. A method of calculating a derived cetane number of a liquid hydrocarbon sample, the method comprising:
    (a) injecting a sample into a combustion chamber, the combustion chamber being held at a constant volume;
    (b) combusting the sample in the combustion chamber;
    (c) measuring a pressure in the constant volume combustion chamber as a function of time after the injection until combustion is completed;
    (d) obtaining a pressure versus time combustion profile of the sample injected into said constant volume combustion chamber, wherein the profile comprises a first region and a second region, the first region including the start of combustion, and the second region relating to a later time than the first region;
    (e) selecting a single data point from the second region of the combustion profile, said data point representing a combustion delay of the combustion profile; and
    (f) calculating the derived cetane number for the sample using the time value associated with said single data point; and wherein the method further comprises the step of performing a blockage check, the blockage check comprising:
    (i) opening the combustion chamber;
    (ii) measuring the pressure in the chamber over time until a pre-determined pressure is reached;
    (iii) determining the time, t1, between opening the chamber and the chamber reaching the predetermined pressure;
    (iv) comparing t1 to a pre-specified threshold time, tt; and
    (v) providing an indication if t1>tt.

11. The method of claim 1, wherein the combustion delay is defined as an elapsed time between injection of the sample, and a time at which a midpoint of a net pressure increase of the combustion profile is reached.

* * * * *